United States Patent
Goshoo et al.

(10) Patent No.: US 9,625,384 B2
(45) Date of Patent: Apr. 18, 2017

(54) DRYNESS FRACTION DISTRIBUTION MEASURING DEVICE AND DRYNESS FRACTION DISTRIBUTION MEASURING METHOD

(71) Applicant: Azbil Corporation, Tokyo (JP)

(72) Inventors: Yasuhiro Goshoo, Tokyo (JP); Giichi Nishino, Tokyo (JP); Shiko Tanabe, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 24 days.

(21) Appl. No.: 14/765,658

(22) PCT Filed: Jan. 30, 2014

(86) PCT No.: PCT/JP2014/052038
§ 371 (c)(1),
(2) Date: Aug. 4, 2015

(87) PCT Pub. No.: WO2014/119641
PCT Pub. Date: Aug. 7, 2014

(65) Prior Publication Data
US 2015/0369736 A1     Dec. 24, 2015

(30) Foreign Application Priority Data
Feb. 4, 2013  (JP) ................................ 2013-019540

(51) Int. Cl.
*G01N 21/00* (2006.01)
*G01N 21/59* (2006.01)
(Continued)

(52) U.S. Cl.
CPC ......... *G01N 21/59* (2013.01); *G01N 21/3554* (2013.01); *G01N 2021/354* (2013.01); *G01N 2201/08* (2013.01)

(58) Field of Classification Search
CPC ......... G01N 2021/354; G01N 21/3554; G01N 21/59; G01N 2201/08
(Continued)

(56) References Cited

U.S. PATENT DOCUMENTS 4,969,115 A  * 11/1990 Rosenthal ............ G01N 21/359
                                                      250/252.1
2012/0147375 A1* 6/2012 Nishino ............... G01N 21/314
                                                      356/437

FOREIGN PATENT DOCUMENTS

| JP | H08-312908 A | 11/1996 |
| JP | 2005-156438 A | 6/2005 |
| JP | 2012-122961 A | 6/2012 |

OTHER PUBLICATIONS

International Search Report and Written Opinion dated Apr. 28, 2014 which issued during the prosecution of International Application No. PCT/JP2014/052038.

* cited by examiner

*Primary Examiner* — Tri T Ton
(74) *Attorney, Agent, or Firm* — Troutman Sanders LLP

(57) ABSTRACT

A dryness fraction measuring device, including a variability quantity measuring portion that measures the amount of variability in intensity of light that has been transmitted, or amount of light that has been absorbed, by moist steam that is the subject of measurement; and a dryness fraction measuring portion that measures the dryness fraction of the moist steam based on a correlation relationship between the dryness fraction and the amount of variability in the optical intensity or in the amount of light absorption.

3 Claims, 11 Drawing Sheets

(51) Int. Cl.
*G01N 21/3554* (2014.01)
*G01N 21/3504* (2014.01)

(58) Field of Classification Search
USPC .................................................. 356/432–444
See application file for complete search history.

1: Dryness Fraction Measuring Device

1b: Dryness Fraction Measuring Device

1c: Dryness Fraction Measuring Device

DRYNESS FRACTION DISTRIBUTION MEASURING DEVICE AND DRYNESS FRACTION DISTRIBUTION MEASURING METHOD

CROSS-REFERENCE TO RELATED APPLICATIONS

This is a U.S. national phase application under 35 U.S.C. §371 of International Patent Application No. PCT/JP2014/052038, filed on Jan. 30, 2014, and claims benefit of priority to Japanese Patent Application No. JP 2013-019540, filed on Feb. 4, 2013. The International Application was published on Aug. 7, 2014, as International Publication No. WO 2014/119641 under PCT Article 21(2). The entire contents of these applications are hereby incorporated by reference.

FIELD OF TECHNOLOGY

The present invention relates to a moist steam measuring technology, relating to a dryness fraction measuring device and dryness fraction measuring method.

BACKGROUND

After water reaches its boiling point, it becomes moist steam that is a mixture of water vapor gas (the gas phase part: saturated vapor) and water droplets (the liquid phase part: saturated water). Here the weight ratio of the water vapor gas relative to the moist steam is termed the "dryness fraction." For example, if water vapor gas and water droplets exist at half each, then the dryness fraction would be 0.5. Moreover, when there are no water droplets but instead there is only water vapor gas, then the dryness fraction would be 1.0. From the perspective of efficiency of use of the apparent heat and latent heat within the moist steam in heat exchanging equipment, and the like, from the perspective of preventing corrosion of turbine blades in steam turbines, and so forth, it is desirable that the dryness fraction of the moist steam be brought to near 1.0. Because of this, a variety of methods have been proposed whereby to measure the moist steam.

For example, Japanese Unexamined Patent Application Publication 8-312908 (JP '908) discloses a technology for calculating the dryness fraction by calculating the saturated hydraulic entropy and the saturated steam entropy using a saturated steam table based on the dry steam flow rates and pressures before and after a pressure regulating valve, taking advantage of the fact that there is no change in total entropy across a pressure regulating valve that is disposed in a pipe.

However, in the technology disclosed in JP '908, it is necessary for the time constant for the sensor for detecting the flow rate and pressure of the moist steam to be long, and necessary to cause the moist steam that is to be measured to undergo a state change from the two-phase state to the gas phase state, and also necessary to stabilize, in the gas phase state, that which is to be measured, and thus there is a problem in that measuring the dryness fraction is time-consuming. Because of this, while it is possible to measure the dryness fraction when the moist state is in a steady state, this cannot be applied to measuring the dryness fraction when the moist steam is in a transient state, prior to becoming stable.

Given this, one aspect of the present invention is to measure the dryness fraction when the moist steam is in a transient state.

Note that there is no limitation to this aspect, but rather enabling means of resolution having the principle of resolution illustrated in the examples below is positioned as another aspect of the present invention.

SUMMARY

The inventor in the present application arrived at the invention of a technology for measuring the dryness fraction using a correlation relationship, through discovering that there is a strong correlation between the dryness fraction of moist steam and variability in the intensity of light transmitted or amount of light absorbed by moist steam, as a result of diligent research into technologies for measuring dryness fractions when moist steam is in an unstable, transient state. Specifically, in order to solve the issues set forth above, the present invention comprises the following structural aspects.

The dryness fraction measuring device according to the present invention has a variability quantity measuring portion for measuring the amount of variability in the intensity of light that passes through the moist steam that is the subject of the measurement, or the amount of variability in the absorbed light; and a dryness fraction measuring portion for measuring the dryness fraction of the moist steam based on a correlation relationship between the dryness fraction and denied a variability in the intensity of light or in the light absorption.

The dryness fraction measuring method according to the present invention includes: illuminating moist steam with light, detecting the amount the intensity of light that passes through the moist steam, and measuring the dryness fraction of the moist steam based on a correlation relationship between the dryness fraction and denied a variability in the intensity of light or in the light absorption.

The present invention may also be provided with the following structures, as desired:

In the invention set forth above, provision of a pressure measuring portion for measuring a pressure of the moist steam, where the correlation relationship is a correlation relationship between the dryness fraction and the amount of variability in the intensity of light or in the light absorption, corresponding to a pressure of the moist steam.

In the invention set forth above, provision of a temperature measuring portion for measuring a temperature of the moist steam, where the correlation relationship is a correlation relationship between the dryness fraction and the amount of variability in the intensity of light or in the light absorption, corresponding to a temperature of the moist steam.

In the invention set forth above, the provision of a light-emitting portion for illuminating with light moist steam that is subject to measurement, the light-receiving portion for detecting light that is passed through the moist steam, an optical intensity measuring portion for measuring the intensity of the light that has been detected, and a correlation relationship storing portion for storing a correlation relationship between the dryness fraction and the amount of variability in the intensity of the light or in the absorption of light, wherein the dryness fraction measuring portion measures the dryness fraction of the moist steam through referencing the correlation relationship stored in the correlation relationship storing portion using, as a reference value, the amount of variability in the measured optical intensity or amount of light absorbed.

The present invention enables measurement of the dryness fraction of moist steam, even when the moist steam is in a transient state, based on the correlation relationship between the dryness fraction and the variability in the optical intensity or the amount of light absorbed.

DETAILED DESCRIPTION

Figure 1:
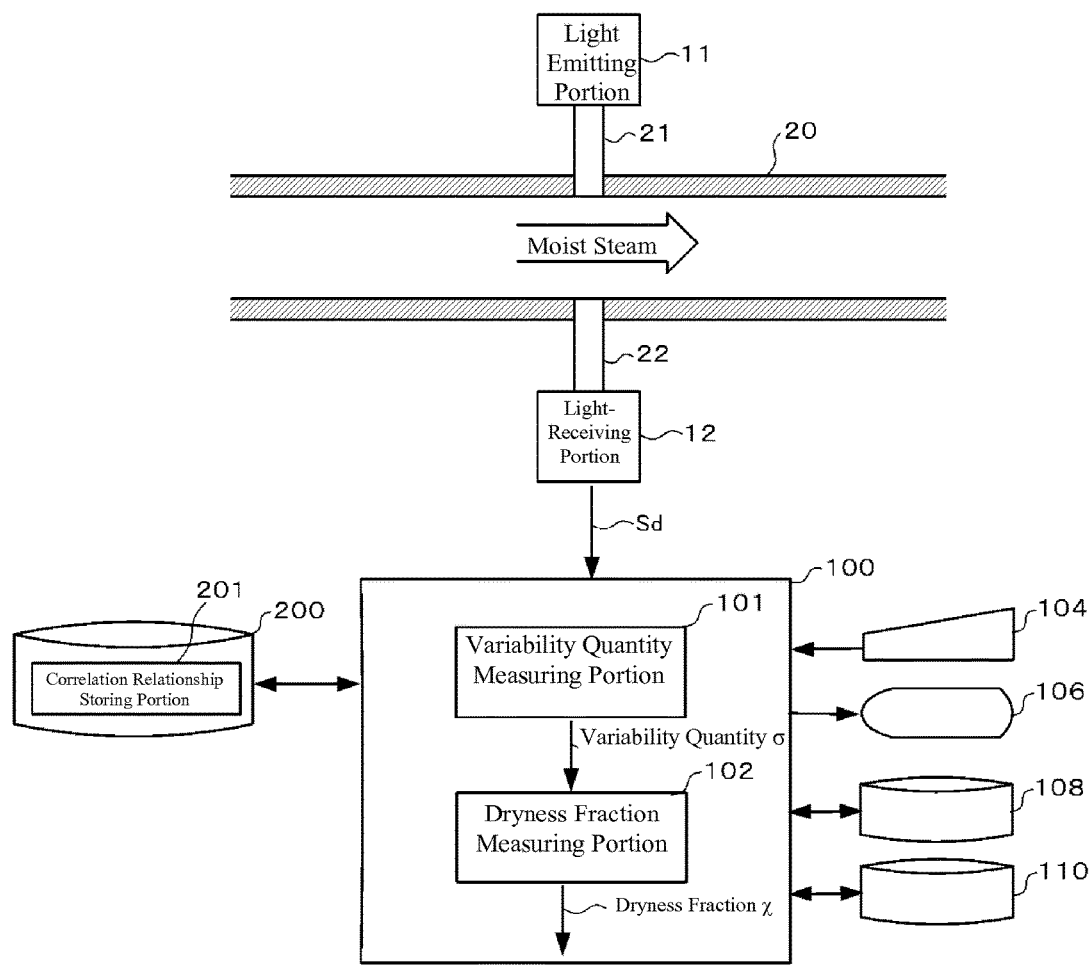
FIG. 1 is a schematic diagram illustrating a dryness fraction measuring device according to an Example according to the present disclosure.

An example according to the present disclosure will be explained below in reference to the drawings. However, the example explained below is no more than an illustration, and is not intended to exclude various modifications and applications to technologies not explicated below. That is, the present disclosure can be exemplified in a variety of modified forms (such as combinations of individual examples), in the scope that does not deviate from the spirit and intent thereof. In the descriptions of the drawings below, identical or similar components are assigned identical or similar codes. The drawings are schematic, and do not necessarily match actual dimensions, ratios, or the like. Furthermore, even within these drawings there may be portions having differing dimensional relationships and proportions.

Definitions

Key terminology used in the present Specification is defined as follows:

"Steam": In each of the examples, this refers to water vapor, but is not limited to water vapor, but may also be a steam that is a substance that is in a two-phase state, with a gas phase part and a liquid phase part.

"Dryness Fraction": This refers to the mass proportion of the gas phase parts and the liquid phase parts within the steam. The dryness fraction as the relationship of dryness fraction (%)=100% (%)−moist fraction (%).

"Moist Steam": This refers to steam wherein the dryness fraction $\chi$ is between 0 and 100(%).

"Saturated Vapor": This refers to the gas phase part of moist steam. This may also be termed dry saturated vapor (saturated dry steam).

"Saturated Water": This refers to the liquid phase part of moist steam.

"Light Intensity" (Optical Intensity): This refers to a physical quantity that represents the intensity of light (the electromagnetic signal), but there is no limitation to this term or to the units used. This is a physical quantity that can be converted between the various units for radiation strength, brightness, photon flux density, etc.

"Amount of Light Absorption": This is a dimensionless quantity indicating the degree with which the optical intensity is weakened when the light passes through the moist steam, also termed "optical density." Despite being termed the "amount of light absorption," this is not limited to the absorption of light, but also includes weakening of the optical intensity through scattering and reflection.

"Variability Quantity": There is no limitation to being a value wherein a difference from a measured value for the optical intensity or the amount of light absorption, which is the population, but rather, in the present invention, is indicated by the "standard deviation" which is expressed by the root mean square of the variance in the population.

Explanation of the Principles Supporting the Invention

First the principle behind the present invention will be explained in reference to FIG. 2 to FIG. 5.

As described above, the present inventor, as a result of diligent research into technologies for measuring the dryness fraction of moist steam in an unstable, transient state, discovered that there is a strong correlation relationship between the dryness fraction of moist steam and the variability in the intensity of light that is transmitted through the moist steam, or the amount of light absorption thereof.

When moist steam flows in a pipe, there will be a gradient within the pipe, depending on the flow speed of the moist steam, between the liquid phase part of the moist steam (the saturated water) and the gas phase part (the saturated vapor). It was discovered that when a transmission path is provided for light at the sidewall of such a pipe and light is transmitted in the crosswise direction, perpendicular to the direction of flow of the moist steam, and the optical intensity that is transmitted through the moist scene is measured, there is a strong correlation relationship between the dryness fraction of the moist steam within the pipe and the amount of variability in the optical intensity.

Figure 2:
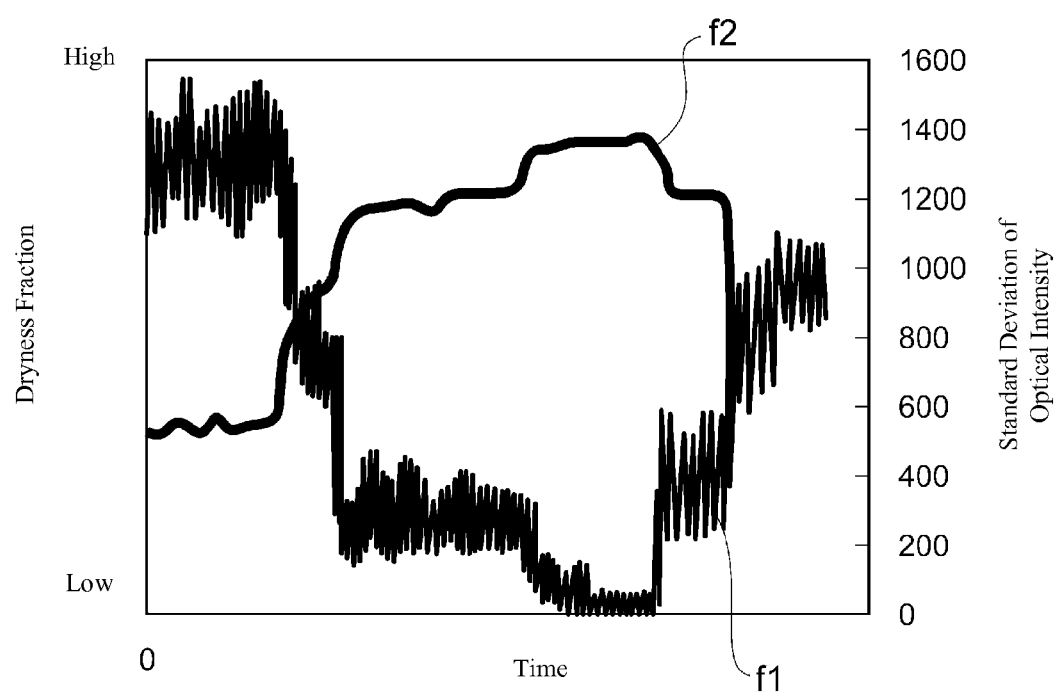
FIG. 2 illustrates a correlation relationship showing the standard deviation of the intensity of light that passes through moist steam, and the dryness fraction of the moist steam corresponding thereto, changing over time.

FIG. 2 illustrates a correlation relationship showing the standard deviation of the intensity of light that passes through moist steam, and the dryness fraction of the moist steam corresponding thereto, changing over time.

In FIG. 2, the curve f1 is the standard deviation. The standard deviation is a plot of the amount of variability in the optical intensity that is transmitted through the moist steam through calculating the standard deviation by acquiring 100 continuous samples at prescribed unit intervals of, for example, about 300 ms, with the total interval of about 30 seconds being a single unit. As illustrated in FIG. 2, the variability of the optical intensity (the standard deviation) varies from moment to moment depending on the state of the moist steam within the pipe. On the other hand, the curve f2 in FIG. 2 is a plot of the measurement of the dryness fraction of the moist steam within the pipe on the same time axis.

When the curve f1 regarding the amount of variability in the optical intensity and the curve f2 regarding the dryness fraction of the moist steam are compared, it can be seen that the greater the amount of variability in the optical intensity (the larger the standard deviation), the smaller the dryness fraction of the moist steam, and that the smaller the amount of variability in the optical intensity (the smaller the standard deviation), the greater the dryness fraction in the moist steam. Moreover, it appears as though there is a correspondence wherein the change in the dryness fraction of the moist steam corresponds to the change in the amount of variability of the optical intensity.

Figure 3:
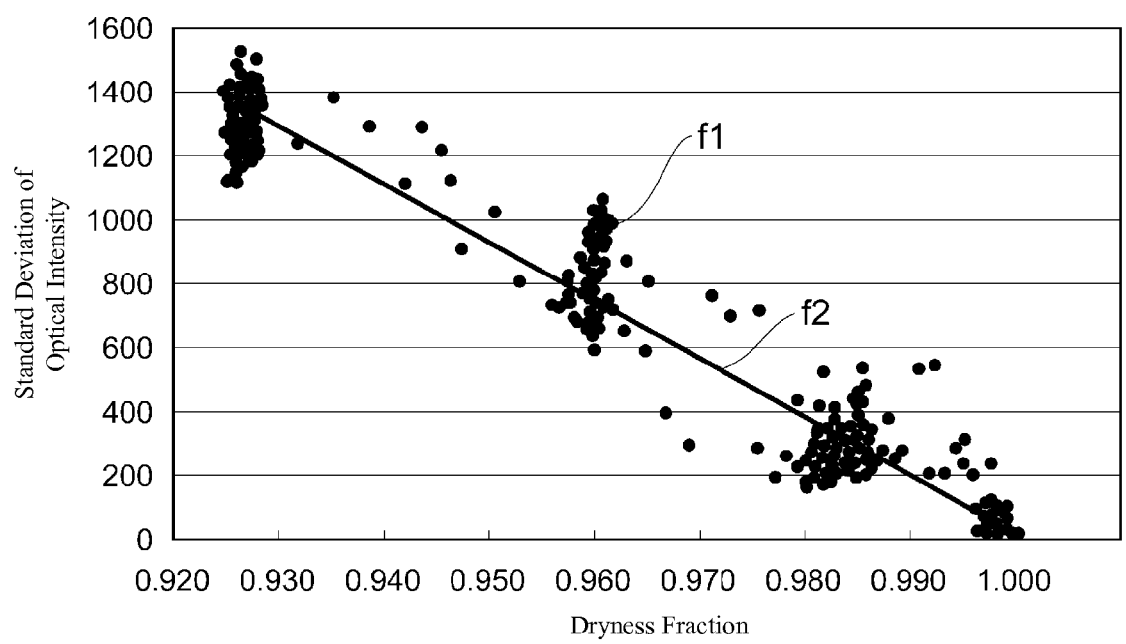
FIG. 3 is a diagram illustrating the correlation relationship between the dryness fraction of the moist steam and the standard deviation of optical intensity in the Example according to the present invention.

When here these two parameters are plotted on perpendicular axes in order to investigate the relationship between the dryness fraction of the moist steam and the amount of variability in the optical intensity, a relationship can be seen as illustrated in FIG. 3.

FIG. 3 is a diagram illustrating the correlation relationship between the dryness fraction of the moist steam and the standard deviation of optical intensity. In FIG. 3, the curve f1 relating to the amount of variability (the standard deviation) of the optical intensity as a function of the dryness fraction is indicated by the set of points, where the curve f2, wherein the curve f1 regarding the amount of variability in the optical intensity is approximated as a straight line, is indicated by a straight line. As illustrated in FIG. 3, a relationship is illustrated wherein the amount of variability (the standard deviation) of the optical intensity increases as the dryness fraction of the moist steam is reduced, and the amount of variability in the optical intensity decreases as the dryness fraction of the moist steam increases, where the dryness fraction of the moist steam can be seen to have a linear first-order correlation relationship with the transmitted optical intensity.

Note that while the existence of a first-order correlation relationship between the dryness fraction of the moist steam and the amount of variability of the optical intensity is illustrated in FIG. 3, there is no limitation thereto. Depending on the state of the moist steam and on the measurement parameters, such as the method for detecting the light, the existence of correlation relationships other than linear correlations can be considered. The present invention is applicable insofar as the relationship between the dryness fraction of the moist steam and the amount of variability has a consistent correlation relationship (for example, a high-order correlation, a logarithmic exponential correlation, or the like) that can be confirmed experimentally.

Figure 4:
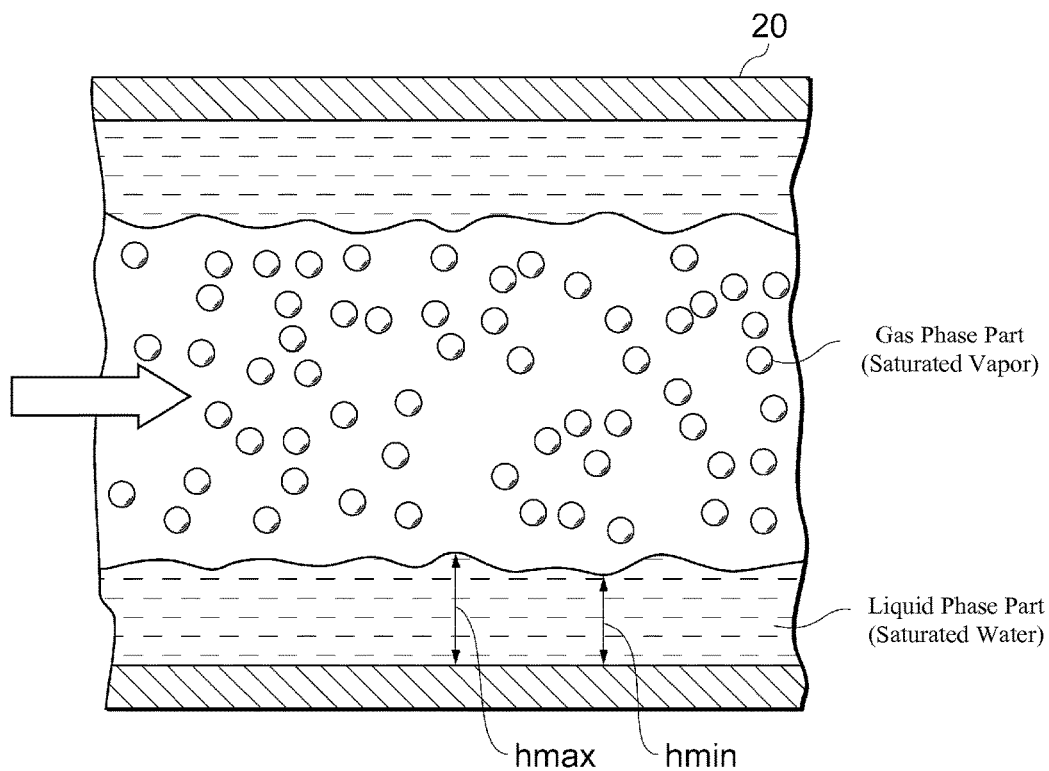
FIG. 4 is a schematic diagram of a pipeline cross section when the liquid phase part of the moist steam is relatively large.
Figure 5:
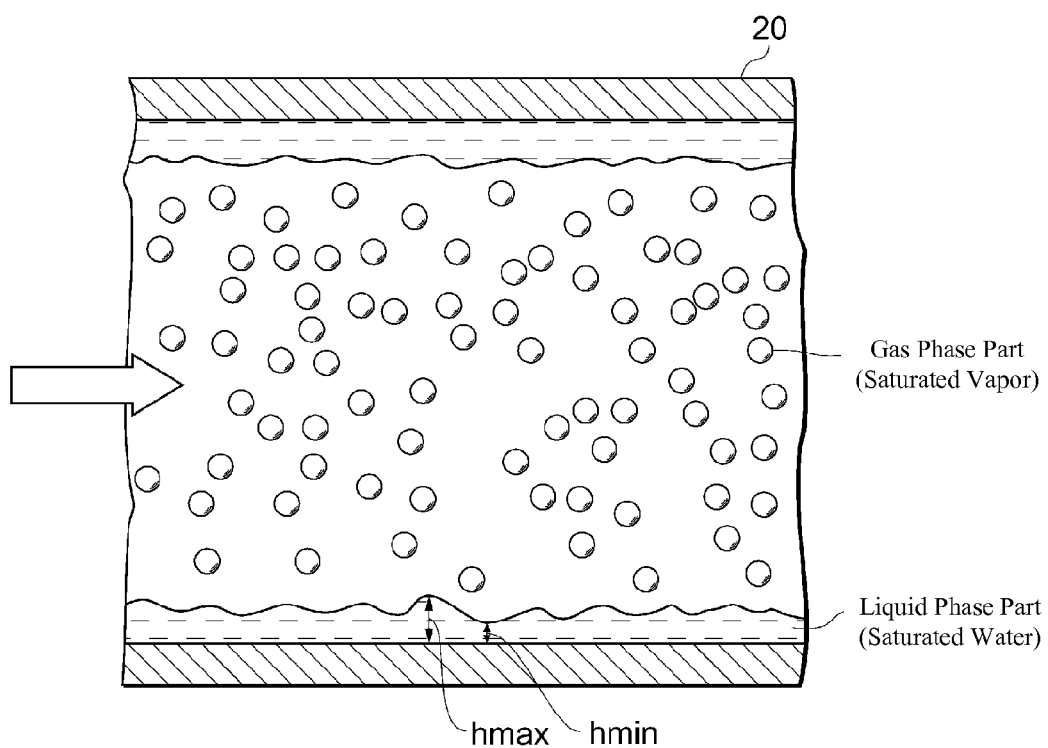
FIG. 5 is a schematic diagram of a pipeline cross section when the liquid phase part of the moist steam is relatively small.

Note that this phenomenon is that as the dryness fraction of the moist steam increases, the amount of variability in the optical intensity will increase when the amount of the liquid phase part (the saturated water) in moist steam increases, and when the dryness fraction of the moist steam decreases, the amount of variability in the optical intensity will decrease when the amount of the liquid phase part of the moist steam decreases, as can be understood from a model such as in FIG. 4 and FIG. 5.

FIG. 4 is a schematic diagram of a pipeline cross section when the liquid phase part of the moist steam is relatively large, and FIG. 5 is a schematic diagram of a pipeline cross section when the liquid phase part of the moist steam is relatively small. As illustrated in FIG. 4 and FIG. 5, when there is moist steam and a substantial flow speed, then the liquid phase part (the saturated water) in the moist steam will flow along the inner wall of the pipe 20, with the flow of the gas phase part (the saturated vapor) concentrating near is the center of the pipe 20.

Here, as illustrated in FIG. 4, when the liquid phase part of the moist steam is relatively large, that is, when the dryness fraction in the moist steam is low, then the thickness of the liquid phase part that is formed on the inner wall surface of the pipe 20 (the height when viewed from the inner wall surface) will become a large. When the thickness of the liquid phase part becomes large, then, as illustrated in FIG. 4, there will be relatively large ripples on the surface of the liquid phase part, creating a large difference between the maximum value hmax and the minimum value hmin in the height of the liquid phase part. It can be understood that when moist steam in this state is illuminated with light from the direction of the diameter of the pipe 20, the intensity of the light that passes through the moist steam will change correspondingly with the height of the liquid phase part, and thus when there is a large difference between the maximum value hmax and the minimum value hmin of the height of the liquid phase part, and there will be a commensurately large amount of variability in the optical intensity.

On the other hand, as illustrated in FIG. 5, when the liquid phase part of the moist steam is relatively small, that is, when the dryness fraction of the moist steam is high, then the thickness of the liquid phase part that is formed on the inner wall surface of the pipe 20 will be small. When the thickness of the liquid phase part is thin, then the ripples produced at the surface of the liquid phase part will be small, so the difference between the maximum value hmax and the minimum value hmin of the height of the liquid phase part will be small. The intensity of light that is transmitted through the diameter direction of the pipe 20 through the moist steam in this state will correspond to the relatively small difference between maximum value hmax and the minimum value hmin for the height of the liquid phase part, so it can be understood that the amount of variability in the optical intensity will be small.

Note that the cross-sectional diagrams illustrated in FIG. 4 and FIG. 5 are merely a model that is simplified for understanding this phenomenon, and there is no limitation to the these illustrations. The phase states of the moist steam that flows within the pipe undergo various changes depending on the flow speed, the dryness fraction, the temperature, and the pressure. Regardless of the type of variation in the phase states of the moist steam, it should be understood that there is a correlation relationship between the dryness fraction of the moist steam and the amount of variability in that the optical intensity.

Moreover, typically the phase states of the moist steam are affected by the pressure of the moist steam, and thus the correlation relationship between the amount of variability in the optical intensity and the dryness fraction of the moist steam will also be affected by the pressure of the moist steam.

Moreover, typically the phase states of the moist steam are affected by the temperature of the moist steam as well, and thus the correlation relationship between the amount of variability in the optical intensity and the dryness fraction of the moist steam will also be affected by the temperature of the moist steam.

Moreover, as explained above, while reference has been made to the relationship between the intensity of light transmitted through the moist steam and the dryness fraction of the moist steam, because the light is absorbed, reflected, and scattered by the moist steam, the amount of light absorbed will also change commensurately with the change in the optical intensity. Consequently, it can be understood that there will be a correlation relationship, similar to the above, between the dryness fraction of the moist steam and the variability in the amount of light absorbed.

An example of the present invention, earnestly proposed by the present inventor in contemplation of the principles described above, will be explained below. In Example, a dryness fraction measuring device that is based on the variability in optical intensity in a state wherein no consideration is given to the effects of pressure and temperature of the moist steam will be explained below. In Another Example, the explanation will be for a dryness fraction measuring device in a case wherein the pressure of the moist steam is taken into consideration. In Yet Another Example, a dryness fraction measuring device in a case wherein the temperature is consideration will be explained. In Further Example, a dryness fraction measuring device that is based on the amount of variability in the amount of light absorption will be explained.

Example

The Example relates to a dryness fraction measuring device for measuring the dryness fraction based on the correlation relationship between the dryness fraction and the variability of the optical intensity transmitted through moist steam. In particular, in the Example the explanation will be for measuring the dryness fraction in a case wherein there is no need to take into account the effects of the pressure and temperature of the moist steam, for example, when performed under conditions for both the pressure and the temperature of the moist steam wherein they will not have any large effect on the amount of variability of the optical intensity.

Structure

FIG. 1 illustrates the structure of a dryness fraction measuring device 1 according to Example. As illustrated in FIG. 1, the dryness fraction measuring device 1 according to the Example is a device for measuring the dryness fraction of moist steam based on the intensity of light that is transmitted through the moist steam that is subject to measurement, which, by way of illustration, is structured including a light-emitting portion 11, a light-receiving portion 12, a variability quantity measuring portion 101, a dryness fraction measuring portion 102, and a storing device 200.

When it comes to the light-emitting portion 11 and the light-receiving portion 12 in the structure set forth above, these are optional structures because arbitrary structures may be used insofar as they are able to output physical quantities corresponding to the intensity of light that has passed through the moist steam.

Moreover, the variability quantity measuring portion 101 and dryness fraction measuring portion 102 in the structural elements set forth above are functional blocks that are implemented functionally through execution of a prescribed software program on a computing device 100. The computing device 100 comprises, for example, an inputting device 104, an outputting device 106, a program storing device 108, a temporary storing device 110, and a storing device 200.

The inputting device 104 is an input portion by which an operator inputs prescribed instructions. As example of the inputting device 104 there are a switch, a keyboard, and the like. The outputting device 106 is an output portion by which the processing results of the computing device 100 are shown to the operator. As examples of the outputting device 106 there are an optical indicator, a digital indicator, a liquid crystal display device, and the like. The outputting device 106 displays, for example, a dryness fraction x, or the like, for the moist steam within the pipe 20, calculated by the dryness fraction measuring portion 102. The program storing device 108 is a memory for storing a software program for causing the computing device 100 to function as the aforementioned functional blocks. The temporary storing device 110 is a memory for storing data temporarily when the computing device 100 executes a software program.

The storing device 200 is a memory that is connected so as to enable referencing by the computing device 100, and is provided with a correlation relationship storing portion 201. The correlation relationship storing portion 201 has a storing region for storing a correlation relationship table that is the correlation relationship between the variability quantity σ (standard deviation) of the optical intensity and the dryness fraction χ of the moist steam, required when the dryness fraction measuring portion 102 executes a calculating procedure. The correlation relationship storing portion 201 is an optional structure because it can be replaced with a relationship equation, described below.

The light-emitting portion 10 is light emitting portion that emits light of a prescribed wavelength. For example, as examples of the light-emitting portion 11 there are a light-emitting diode, a super-luminescent diode, a semiconductor laser, a laser oscillator, a fluorescent discharge tube, a low-pressure mercury lamp, a xenon lamp, and the like.

An optical waveguide 21 may be connected to the light-emitting portion 11. The optical waveguide 21 is provided passing through a side wall of the pipe 20, or is connected to a transparent window that is provided in the sidewall of the pipe 20, or the like. For example, the light that is carried by the optical waveguide 21 enters into the pipe 20 from the end portion of the optical waveguide 21. While plastic optical fibers made out of poly methyl methacrylate (PMMA), glass optical fibers made out of quartz glass, or the like, may be used in the optical waveguide 21, there is no limitation thereto insofar as it is capable of carrying the light that is produced by the light-emitting portion 11.

The pipe 20 is a pipe through which the moist steam, which is the subject of the measurement, passes. An optical waveguide 22 into which light that has been emitted from the optical waveguide 21, described above, and that has passed through the moist steam within the pipe 20, is incident may be connected to the pipe 20. The optical waveguide 22 is provided passing through a side wall of the pipe 20, or is connected to a transparent window that is provided in the sidewall of the pipe 20, or the like. An end portion of the optical waveguide 22 faces an end portion of the optical waveguide 21 in the radial direction of the pipe 20. The optical waveguide 22 is structured so as to be able to guide, to the photodetecting portion 12, the light that has traversed the moist steam within the pipe 20.

The light-receiving portion 12 is a photodetecting portion that detects light that has passed through the moist steam within the pipe 20. For example, a photodiode, a phototransistor, or another photoelectric converting element may be used for the light-receiving portion 12. The light-receiving portion 12 outputs a photodetection signal Sd depending on the intensity of light that has passed through the moist steam.

Note that the light-emitting portion 11 may be provided in proximity, without providing the optical waveguide 21, on the sidewall of the pipe 20, and the light-receiving portion 12 may be provided in the vicinity of the sidewall of the pipe 20 without providing the optical waveguide 22. Moreover, while in FIG. 1 the light-emitting portion 11 and the light-receiving portion 12 are provided facing each other, instead of this, a light-emitting/light-receiving element wherein both the light-emitting portion and the light-receiving portion are integrated together, may be used. When a light-emitting/ light-receiving element is used, a reflective plate may be disposed on the sidewall of the pipe that faces the light-emitting/light-receiving element. The light that is produced by the light-emitting/light-receiving element passes through the interior of the pipe and is reflected by the reflecting plate, to pass into the interior of the pipe and be received by the light-emitting/light-receiving element. Moreover, a known optical measuring instrument, such as a spectrometer wherein an output is produced that corresponds the optical intensity, such as a known spectrometer, or the like, may be used instead of the light-emitting portion 11 and the light-receiving portion 12.

The variability quantity measuring portion 101 is a measuring portion that measures the amount of variability in the intensity of the light that has passed through the moist steam that is subject to measurement. Specifically, the variability quantity measuring portion 101 inputs, from the light-receiving portion 12, the photodetection signal Sd, and after sampling a prescribed number of samples over a prescribed interval, such as sampling the optical intensity, indicated by the photodetection signal Sd for 100 samples at 300 ms intervals, for example, and calculates, as the variability quantity $\sigma$ of the optical intensity, the standard deviation of the light intensity for that number of samples. The sampling interval and number of samples are either the same as when the correlation relationship between the amount of variability in the optical intensity and the dryness fraction that is referenced by the dryness fraction measuring portion 102 was calculated, or must have a correspondence relationship therewith.

The dryness fraction measuring portion 102 is a measuring portion that measures the dryness fraction $\chi$ of the moist theme based on the correlation relationship between the dryness fraction and the amount of variability, stored in the correlation relationship storing portion 201 of the storing device 200. Specifically, the dryness fraction measuring portion 102 references the correlation relationship storing portion 201 of the storing device 200, using, as a reference will value, the variability quantity $\sigma$ measured by the variability quantity measuring portion 101, to acquire, and output as an output value, the dryness fraction $\chi$ that corresponds to the variability quantity $\sigma$ (standard deviation).

The correlation relationships between the moist steam dryness fraction $\chi$ and the variability quantity $\sigma$ (standard deviation) of the light intensity are stored, for example, in a data table, as illustrated in FIG. 3, in the correlation relationship storing portion 201. This correlation relationship indicates the relationship between the dryness fraction of the moist steam and the amount of variability in the optical intensity, at a predetermined pressure and temperature envisioned for the dryness fraction measuring device 1 for the moist steam.

Note that because the correlation relationship between the dryness fraction $\chi$ of the moist heating and the variability quantity $\sigma$ (standard deviation) of the optical intensity has a correlation relationship with a given constant, this relationship can be written using a relationship equation as in Equation (1), below. If the correlation relationship between the dryness fraction $\chi$ for the moist steam in the variability quantity $\sigma$ for the optical intensity has a linear correlation relationship, as illustrated in FIG. 3, then Equation (1) can be written as a linear function approximation.

$$\text{Dryness fraction } \chi = f(\sigma) \quad (1)$$

Consequently, when the relationship equation is used, the dryness fraction measuring portion 102 calculates and outputs the dryness fraction $\chi$ by substituting, into Equation (1) the variability quantity $\sigma$ of the optical intensity.

Operation

The operation of the Example will be explained next.

First, when measuring the dryness fraction of the moist steam in a state wherein moist steam is flowing within the pipe 20, the light-emitting portion 11 is caused to emit light. The light that propagates through the optical waveguide 21 from the light-emitting portion 11 is a method into the moist steam within the pipe 20.

The light that passes through the moist steam is incident into the optical waveguide 22 on the opposite side of the pipe 20, to be detected by the light-receiving portion 12. The light-receiving portion 12 outputs a photodetection signal Sd corresponding to the intensity of light that has passed through the moist steam.

The variability quantity measuring portion 101 references the photodetection signal Sd, to calculate the variability quantity (standard deviation) $\sigma$ from the optical intensity for a predetermined number of samples at a predetermined sampling interval. If the interval for the samples and/or the number of samples is different from when the data table or the relationship equation that show the correlation between the dryness fraction of the moist steam and the variability quantity for the optical intensity, referenced by the dryness fraction measuring portion 102, were created, then the variability quantity $\sigma$ is calculated through a prescribed conversion calculation.

Following this, the dryness fraction measuring portion 102 either references the correlation relationship storing portion 201 of the storing device 200 using, as the reference value, the calculated optical intensity variability quantity $\sigma$, or performs a calculation based on a relationship equation, such as Equation (1), above, to output the corresponding dryness fraction $\chi$ of the moist steam. The dryness fraction $\chi$ of the moist steam, which has been outputted, is, for example, displayed on the outputting device 106.

Effects

Given the Example, explained above, the dryness fraction $\chi$ can be calculated based on the correlation relationship between the dryness fraction $\chi$ of the moist steam and the variability quantity $\sigma$ of the optical intensity, without being effected by the state of the moist steam, thus enabling reliable measurement of the dryness fraction of the moist steam, even when the moist steam is in a transient state.

Another Example

While the Example, described above, explained a dryness fraction measuring device for a case wherein there was no need to take into consideration the effects of the pressure and temperature of the moist steam, Another Example relates to a dryness fraction measuring device that takes the pressure of the moist steam into account.

Structure

Figure 6:
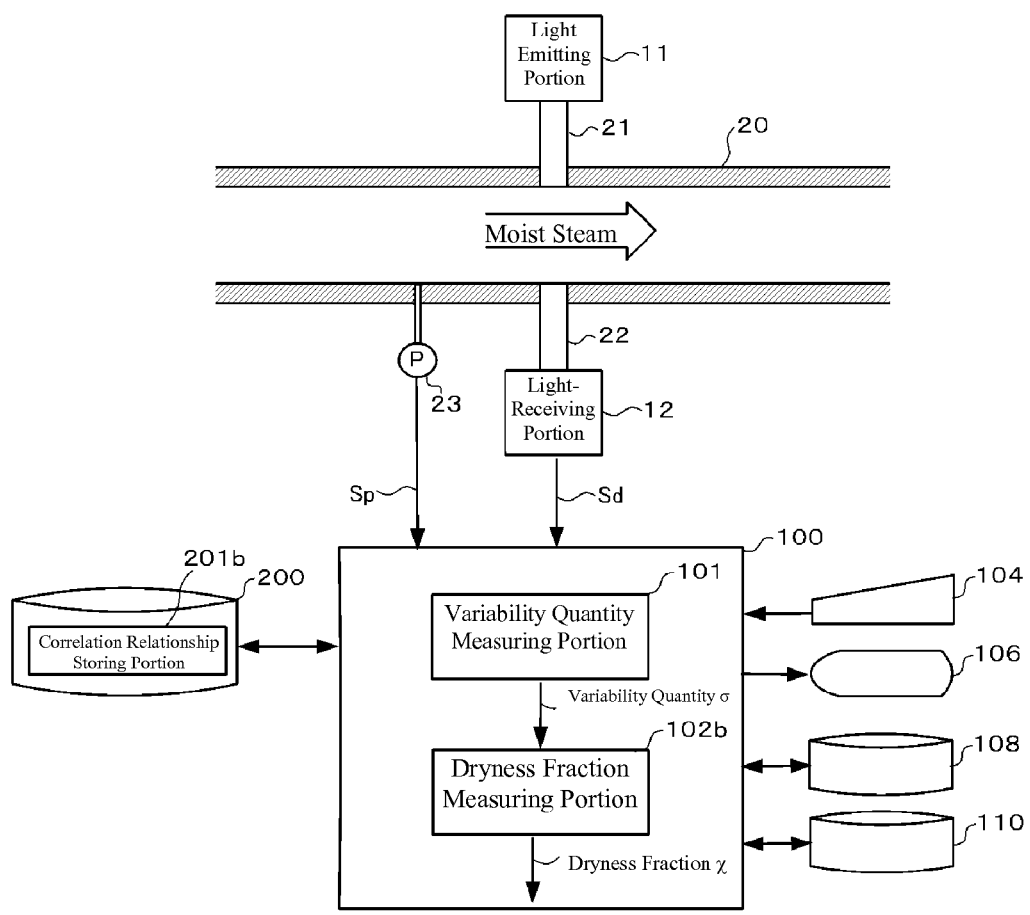
FIG. 6 is a schematic diagram illustrating a dryness fraction measuring device according to Another Example according to the present disclosure.

FIG. 6 illustrates the structure of a dryness fraction measuring device 2b according to Another Example. As illustrated in FIG. 6, the dryness fraction measuring device 1b according to the Another Example is a device for measuring the dryness fraction of moist steam based on the intensity of light that is transmitted through the moist steam, adapted to the pressure of the moist steam that is subject to measurement, which, by way of illustration, is structured including a light-emitting portion 11, a light-receiving portion 12, a variability quantity measuring portion 101, a dryness fraction measuring portion 102b, a correlation relationship storing portion 201b, and a storing device 200.

In the Another Example, a pressure sensor 23 is also provided. The pressure sensor 23 is disposed in the pipe 20, to measure a pressure p of the moist steam within the pipe 20 and to output it to the computing device 100 as a pressure signal Sp.

In the structure described above, the points that the light-emitting portion 11, the light-receiving portion 12, and the correlation relationship storing portion 201*b* are optional structures, and that the variability quantity measuring portion 101 and dryness fraction measuring portion 102*b* in the structural elements set forth above are functional blocks that are implemented functionally through execution of a prescribed software program on a computing device 100, are the same as in the Example, set forth above.

In the Another Example, the points that the correlation relationship storing portion 201*b* of the storing device 200 stores correlation relationship table that indicates the correlation relationship between the variability quantity σ (standard deviation) of the optical intensity and the dryness fraction χ of the moist steam, corresponding to the pressure p of the moist steam, and that the dryness fraction measuring portion 102*b* measures the dryness fraction χ of the moist steam based on the correlation relationship between the amount of variability in the intensity of light and the dryness fraction, corresponding to the pressure of the moist steam, are different from the Example set forth above. The other structures are identical to those in the Example, and thus explanations thereof will be omitted.

Specifically, the dryness fraction measuring portion 102*b* references the correlation relationship storing portion 201*b* of the storing device 200, using, as reference values, the pressure signal Sp that indicates the pressure p of the moist steam, detected by the pressure sensor 23, and the variability quantity σ measured by the variability quantity measuring portion 101, to acquire, and output as an output value, the dryness fraction χ that corresponds to the variability quantity σ (standard deviation), from the correlation relationship corresponding to the pressure p.

Figure 7:
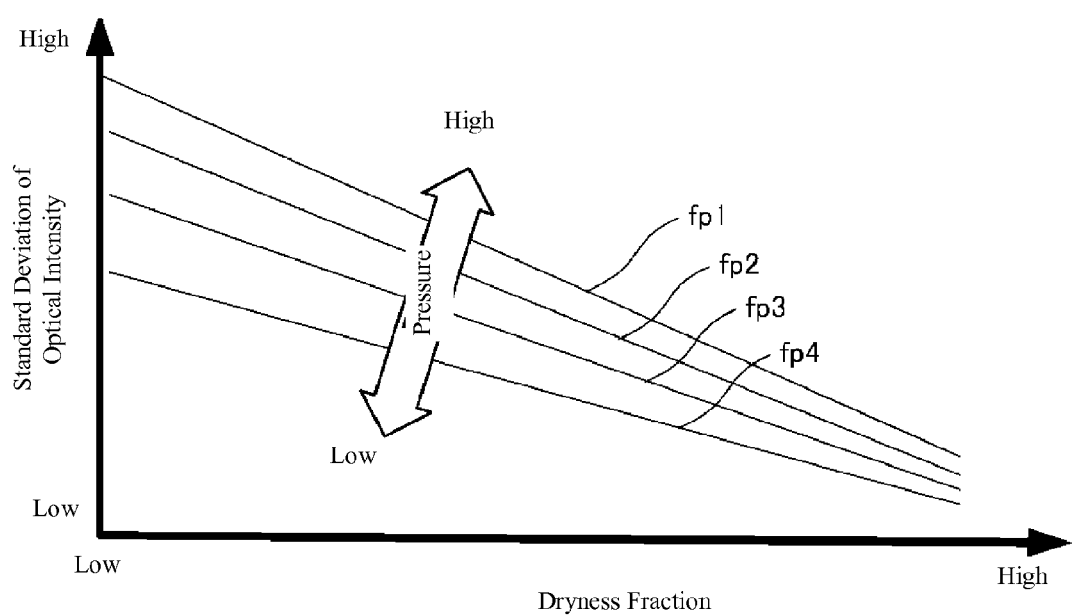
FIG. 7 is a diagram illustrating the correlation relationship between the pressure and dryness fraction of the moist steam and the standard deviation of optical intensity in the Another Example according to the present invention.

The correlation relationship storing portion 201*b* stores, as a data table, a plurality of correlation relationships fP1 through fP4 for the dryness fraction χ of the moist steam and the variability quantity σ (standard deviation) for the optical intensity, corresponding to the magnitudes of the pressure p of the moist steam, as illustrated in FIG. 7, for example. These correlation relationships fP1 through fP4 are illustrative examples of the relationships between the dryness fraction of the moist steam and the amount of variability in the optical intensity for each pressure of the moist steam, for the moist steam that is envisioned for the dryness fraction measuring device 1*b*.

Note that because the correlation relationship between the dryness fraction χ of the moist heating and the variability quantity σ (standard deviation) of the optical intensity, corresponding to the pressure p of the moist steam, has a correlation relationship with a given constant, this relationship can be written using a relationship equation as in Equation (2), below. If the correlation relationship between the dryness fraction χ for the moist steam in the variability quantity σ for the optical intensity for each pressure p has a linear correlation relationship, as illustrated in FIG. 7, then Equation (2) can be written as a linear function approximation.

$$\text{Dryness fraction } \chi = f(\sigma, p) \quad (2)$$

Consequently, when the relationship equation is used, the dryness fraction measuring portion 102*b* and calculates and outputs the dryness fraction χ corresponding to the pressure p of the moist steam by substituting, into Equation (2) the variability quantity σ of the optical intensity.

Operation

The operation of the Another Example will be explained next.

First, when measuring the dryness fraction of the moist steam in a state wherein moist steam is flowing within the pipe 20, the light-emitting portion 11 is caused to emit light. The light that propagates through the optical waveguide 21 from the light-emitting portion 11 is a method into the moist steam within the pipe 20.

The light that passes through the moist steam is incident into the optical waveguide 22 on the opposite side of the pipe 20, to be detected by the light-receiving portion 12. The light-receiving portion 12 outputs a photodetection signal Sd corresponding to the intensity of light that has passed through the moist steam.

The pressure sensor 23 measures a pressure p of the moist steam within the pipe 20 and to outputs it to the computing device 100 as a pressure signal Sp.

The variability quantity measuring portion 101 references the photodetection signal Sd, to calculate the variability quantity (standard deviation) σ from the optical intensity for a predetermined number of samples at a predetermined sampling interval. If the interval for the samples and/or the number of samples is different from when the data table or the relationship equation that show the correlation between the dryness fraction of the moist steam and the variability quantity for the optical intensity, referenced by the dryness fraction measuring portion 102, were created, then the variability quantity σ is calculated through a prescribed conversion calculation.

Following this, the dryness fraction measuring portion 102*b* either references the correlation relationship storing portion 201*b* using, as the reference values, the measured pressure p of the moist steam and the calculated optical intensity variability quantity σ, or performs a calculation based on a relationship equation, such as Equation (2), above, to output the corresponding dryness fraction χ of the moist steam. The dryness fraction χ of the moist steam, which has been outputted, is, for example, displayed on the outputting device 106.

Effects

Given the Another Example, explained above, the dryness fraction χ can be calculated based on the correlation relationship between the dryness fraction χ of the moist steam and the variability quantity σ of the optical intensity, without being effected by the state of the moist steam, thus enabling reliable measurement of the dryness fraction of the moist steam, even when the moist steam is in a transient state.

In particular, in this Another Example, correlation relationships between the dryness fraction χ of the moist steam and the variability quantity σ for the optical intensity, prepared corresponding to pressures p for the moist steam, are used, making it possible to measure the dryness fraction of the moist steam accurately even under conditions wherein the pressure of the moist steam will have an effect on the dryness fraction.

Yet Another Example

In the Another Example, set forth above, the pressure of the moist steam was taking into consideration, but in this Yet Another Example the explanation will be for a dryness fraction measuring device in a case wherein the temperature of the moist steam is taken into consideration.

Structure

Figure 8:
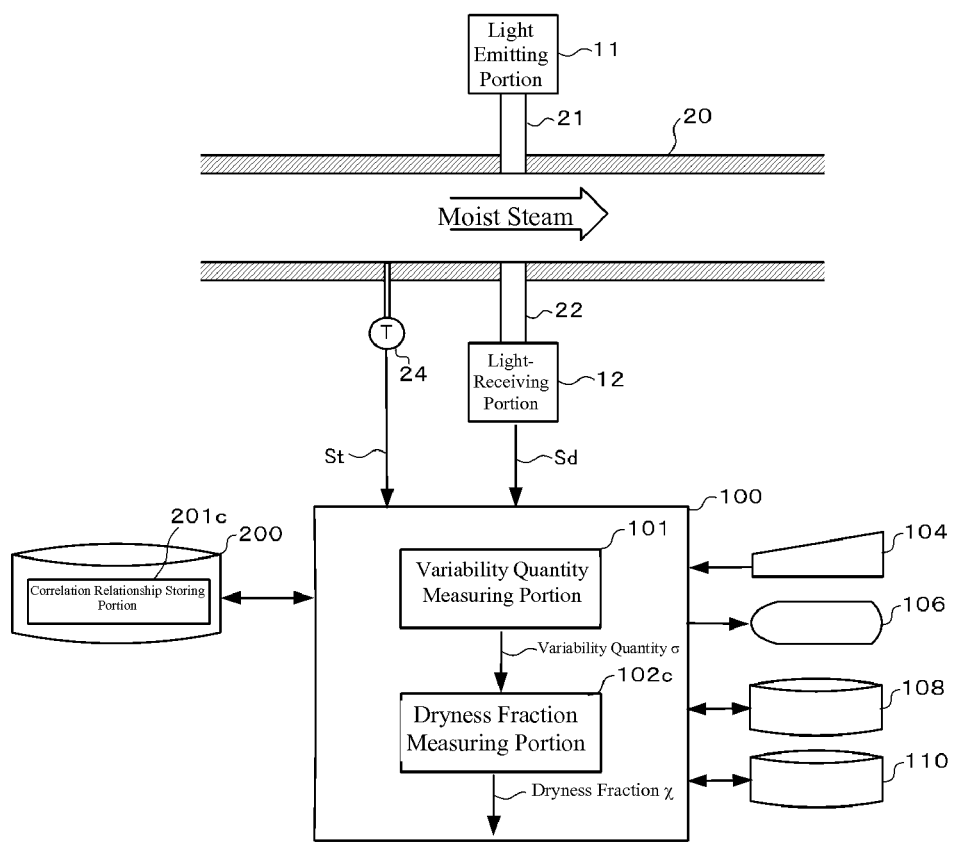
FIG. 8 is a schematic diagram illustrating a dryness fraction measuring device according to Yet Another Example according to the present disclosure.

FIG. 8 illustrates the structure of a dryness fraction measuring device 1*c* according to Yet Another Example. As illustrated in FIG. 8, the dryness fraction measuring device 1*c* according to the Yet Another Example is a device for measuring the dryness fraction of moist steam based on the intensity of light that is transmitted through the moist steam, adapted to the temperature of the moist steam that is subject to measurement, which, by way of illustration, is structured including a light-emitting portion 11, a light-receiving portion 12, a variability quantity measuring portion 101, a dryness fraction measuring portion 102c, a correlation relationship storing portion 201c, and a storing device 200.

In the Yet Another Example, a temperature sensor 24 is also provided. The temperature sensor 24 is disposed in the pipe 20, to measure a temperature t of the moist steam within the pipe 20 and to output it to the computing device 100 as a temperature signal St.

In the structure described above, the points that the light-emitting portion 11, the light-receiving portion 12, and the correlation relationship storing portion 201c are optional structures, and that the variability quantity measuring portion 101 and dryness fraction measuring portion 102c in the structural elements set forth above are functional blocks that are implemented functionally through execution of a prescribed software program on a computing device 100, are the same as in the Example, set forth above.

In the Yet Another Example, the points that the correlation relationship storing portion 201c of the storing device 200 stores correlation relationship table that indicates the correlation relationship between the variability quantity σ (standard deviation) of the optical intensity and the dryness fraction χ of the moist steam, corresponding to the temperature t of the moist steam, and that the dryness fraction measuring portion 102c measures the dryness fraction χ of the moist steam based on the correlation relationship between the amount of variability in the intensity of light and the dryness fraction, corresponding to the temperature of the moist steam, are different from the Example set forth above. The other structures are identical to those in the Example, and thus explanations thereof will be omitted.

Specifically, the dryness fraction measuring portion 102c references the correlation relationship storing portion 201c of the storing device 200, using, as reference values, the temperature signal St that indicates the temperature t of the moist steam, detected by the temperature sensor 24, and the variability quantity σ measured by the variability quantity measuring portion 101, to acquire, and output as an output value, the dryness fraction χ that corresponds to the variability quantity σ (standard deviation), from the correlation relationship corresponding to the temperature t.

Figure 9:
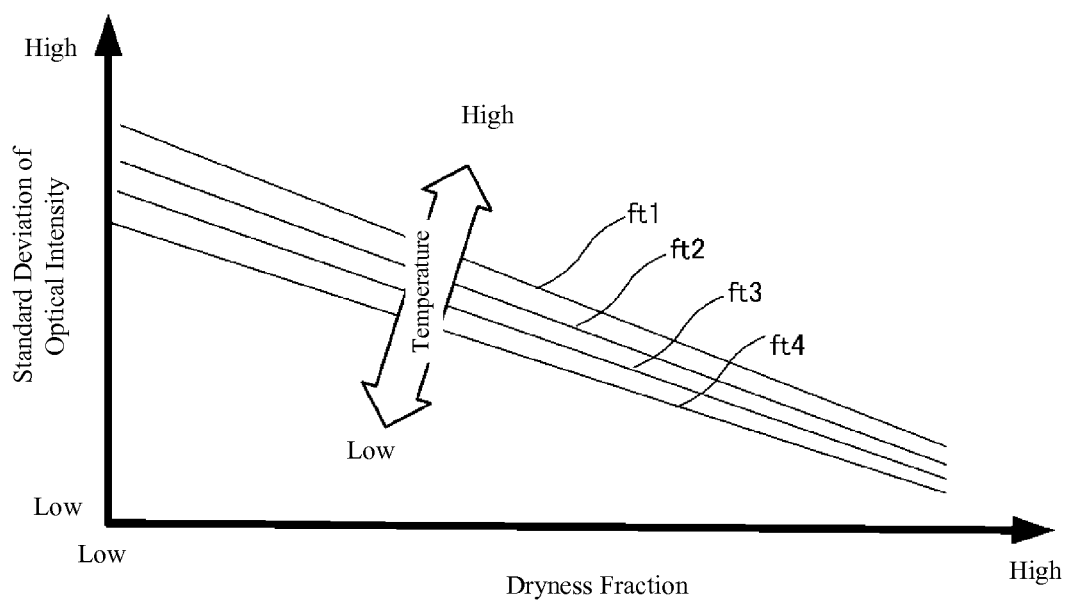
FIG. 9 is a diagram illustrating the correlation relationship between the temperature and dryness fraction of the moist steam and the standard deviation of optical intensity in the Yet Another Example according to the present invention.

The correlation relationship storing portion 201c stores, as a data table, a plurality of correlation relationships ft1 through ft4 for the dryness fraction χ of the moist steam and the variability quantity σ (standard deviation) for the optical intensity, corresponding to the magnitudes of the temperature t of the moist steam, as illustrated in FIG. 9, for example. These correlation relationships ft1 through ft4 are illustrative examples of the relationships between the dryness fraction of the moist steam and the amount of variability in the optical intensity for each temperature of the moist steam, for the moist steam that is envisioned for the dryness fraction measuring device 1b.

Note that because the correlation relationship between the dryness fraction χ of the moist heating and the variability quantity σ (standard deviation) of the optical intensity, corresponding to the temperature t of the moist steam, has a correlation relationship with a given constant, this relationship can be written using a relationship equation as in Equation (3), below. If the correlation relationship between the dryness fraction χ for the moist steam in the variability quantity σ for the optical intensity for each temperature t has a linear correlation relationship, as illustrated in FIG. 9, then Equation (3) can be written as a linear function approximation.

$$\text{Dryness fraction } \chi = f(\sigma, t) \quad (3)$$

Consequently, when the relationship equation is used, the dryness fraction measuring portion 102c and calculates and outputs the dryness fraction χ corresponding to the temperature t of the moist steam by substituting, into Equation (3) the variability quantity σ of the optical intensity.

Operation

The operation of the Yet Another Example will be explained next.

First, when measuring the dryness fraction of the moist steam in a state wherein moist steam is flowing within the pipe 20, the light-emitting portion 11 is caused to emit light. The light that propagates through the optical waveguide 21 from the light-emitting portion 11 is a method into the moist steam within the pipe 20.

The light that passes through the moist steam is incident into the optical waveguide 22 on the opposite side of the pipe 20, to be detected by the light-receiving portion 12. The light-receiving portion 12 outputs a photodetection signal Sd corresponding to the intensity of light that has passed through the moist steam.

The temperature sensor 24 measures a temperature t of the moist steam within the pipe 20 and to outputs it to the computing device 100 as a temperature signal St.

The variability quantity measuring portion 101 references the photodetection signal Sd, to calculate the variability quantity (standard deviation) σ from the optical intensity for a predetermined number of samples at a predetermined sampling interval. If the interval for the samples and/or the number of samples is different from when the data table or the relationship equation that show the correlation between the dryness fraction of the moist steam and the variability quantity for the optical intensity, referenced by the dryness fraction measuring portion 102, were created, then the variability quantity σ is calculated through a prescribed conversion calculation.

Following this, the dryness fraction measuring portion 102c either references the correlation relationship storing portion 201c using, as the reference values, the measured temperature t of the moist steam and the calculated optical intensity variability quantity σ, or performs a calculation based on a relationship equation, such as Equation (3), above, to output the corresponding dryness fraction χ of the moist steam. The dryness fraction χ of the moist steam, which has been outputted, is, for example, displayed on the outputting device 106.

Effects

Given the Yet Another Example, explained above, the dryness fraction χ can be calculated based on the correlation relationship between the dryness fraction χ of the moist steam and the variability quantity σ of the optical intensity, without being effected by the state of the moist steam, thus enabling reliable measurement of the dryness fraction of the moist steam, even when the moist steam is in a transient state.

In particular, in this Yet Another Example, correlation relationships between the dryness fraction χ of the moist steam and the variability quantity σ for the optical intensity, prepared corresponding to temperatures t for the moist steam, are used, making it possible to measure the dryness fraction of the moist steam accurately even under conditions wherein the temperature of the moist steam will have an effect on the dryness fraction.

Further Example

While the Example, Another Example, and Yet Another Example, described above, measured the dryness fraction of the moist steam based on the amount of variability in the intensity of the light, the Further Example relates to a dryness fraction measuring device for measuring the dryness fraction of moist steam based on the variability of the optical the absorption of light.

Structure

Figure 10:
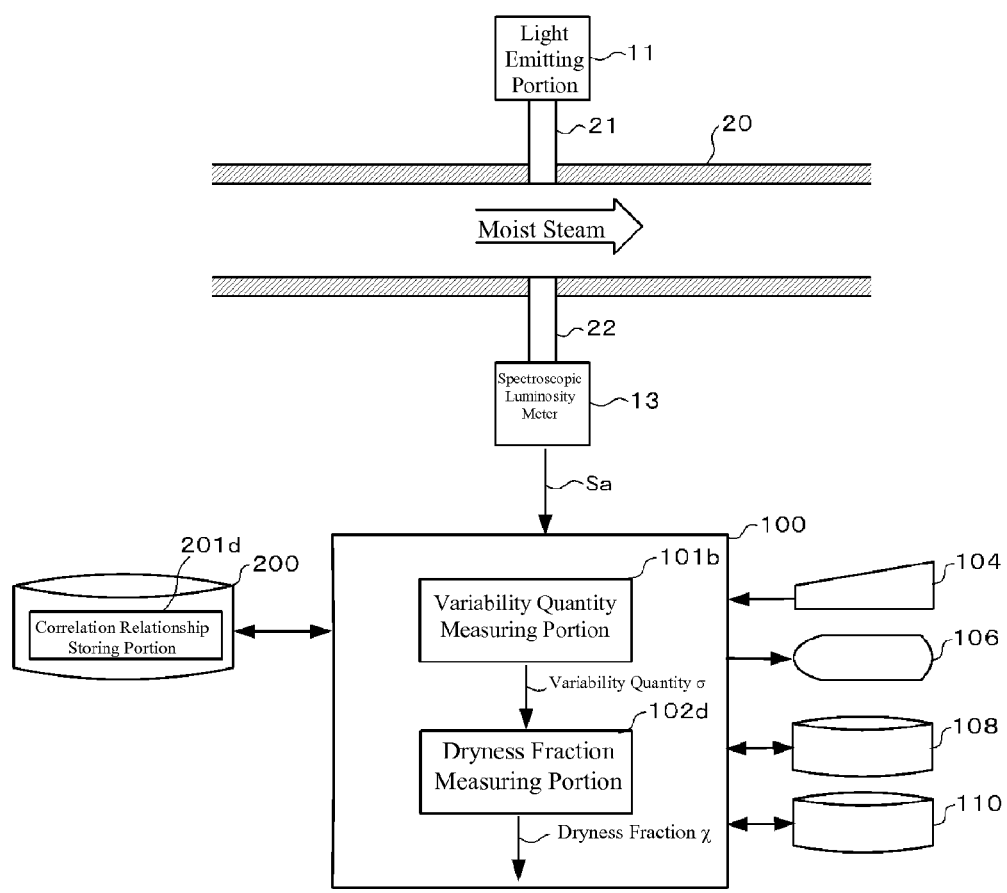
FIG. 10 is a schematic diagram illustrating a dryness fraction measuring device according to a Further Example according to the present disclosure.

FIG. 10 illustrates the structure of a dryness fraction measuring device 1d according to a Further Example. As illustrated in FIG. 10, the dryness fraction measuring device 1d according to the Further Example is a device for measuring the dryness fraction based on the variability of the absorption of light by the moist steam, which, by way of illustration, is structured including a light-emitting portion 11, a light-receiving portion 13, a variability quantity measuring portion 101b, a dryness fraction measuring portion 102, and a storing device 200.

In this Further Example, the point that a spectroscopic luminosity meter 13 is provided instead of the light-receiving portion 12 differs from the examples described above. The spectroscopic luminosity meter 13 is a measuring portion that measures the light absorption, based on the intensity of light that passes through the moist steam.

Moreover, the points that the correlation relationship storing portion 201d of the storing device 200 stores correlation relationship table that indicates the correlation relationship between the variability quantity σ (standard deviation) of the light absorption and the dryness fraction χ of the moist steam, and that the dryness fraction measuring portion 102c measures the dryness fraction χ of the moist steam based on the correlation relationship between the amount of variability in the absorption of light and the dryness fraction, are different from the Example set forth above.

Note, the point that the variability quantity measuring portion 101b and dryness fraction measuring portion 102d in the structure set forth above are functional blocks that are implemented functionally through execution of a prescribed software program on a computing device 100 is the same as in the Example, set forth above.

Specifically, the spectroscopic luminosity meter 13 calculates, and outputs as a light absorption signal Sa, the amount of light absorbed, based on the intensity of light that has passed through the moist steam. If here the incident optical intensity is defined as I0 and the intensity of the light that is detected is defined as I, then the optical absorption A can be defined as in Equation (4):

$$\text{Optical Absorption } A = -\log_{10}(I/I0) \quad (4)$$

Given the above, if it is possible to measure the intensity of light that passes through the moist steam, the optical absorption A will be defined uniquely. Consequently, the computing device 100 is structured so as to input the photo detection signal Sd that includes the intensity of the light, in the same manner as in the Example, Another Example, and Yet Another Example, set forth above, to calculate the optical absorption A based on Equation (4).

The variability quantity measuring portion 101b inputs, from the spectroscopic luminosity meter 13, the optical absorption signal Sa, and after sampling a prescribed number of samples over a prescribed interval, such as sampling the optical intensity, indicated by the optical absorption signal Sa for 100 samples at 300 ms intervals, for example, and calculates, as the variability quantity σ of the optical absorption, the standard deviation of the optical absorption for that number of samples.

The dryness fraction measuring portion 102d references the correlation relationship storing portion 201d of the storing device 200, using, as a reference value, the variability quantity σ for the optical absorption measured by the variability quantity measuring portion 101b, to acquire, and output as an output value, the dryness fraction χ that corresponds to the variability quantity σ (standard deviation) for the optical absorption, from the correlation relationship between the dryness fraction and the amount of variability in the optical absorption.

Figure 11:
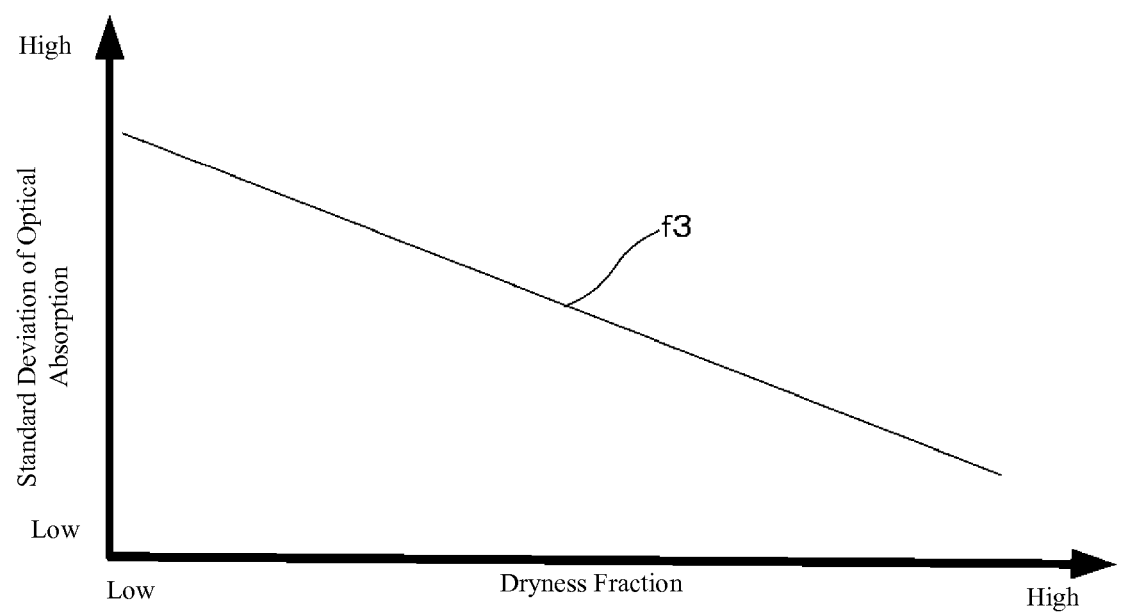
FIG. 11 is a diagram illustrating the correlation relationship between the dryness fraction of the moist steam and the standard deviation of optical absorption in the Further Example according to the present invention.

The plurality of correlation relationship f3 between the moist steam dryness fraction χ and the variability quantity σ (standard deviation) of the optical absorption are stored, for example, in a data table, as illustrated in FIG. 11, in the correlation relationship storing portion 201d. That because the correlation relationship between the dryness fraction χ of the moist heating and the variability quantity σ (standard deviation) of the optical absorption has a correlation relationship with a given constant, this relationship can be written using a relationship equation as in Equation (5), below. If the correlation relationship between the dryness fraction χ for the moist steam in the variability quantity σ for the optical absorption has a linear correlation relationship, as illustrated in FIG. 11, then Equation (5) can be written as a linear function approximation.

$$\text{Dryness fraction } \chi = g(\sigma) \quad (5)$$

Consequently, when the relationship equation is used, the dryness fraction measuring portion 102d calculates and outputs the dryness fraction χ by substituting, into Equation (5) the variability quantity σ of the optical absorption. [95]

Operation

The operation of the Further Example will be explained next.

First, when measuring the dryness fraction of the moist steam in a state wherein moist steam is flowing within the pipe 20, the light-emitting portion 11 is caused to emit light. The light that propagates through the optical waveguide 21 from the light-emitting portion 11 is a method into the moist steam within the pipe 20.

The light that passes through the moist steam is incident into the optical waveguide 22 on the opposite side of the pipe 20, to be detected by the spectroscopic luminosity meter 13. The spectroscopic luminosity meter 13 outputs a light absorption signal Sa that indicates the amount of light absorbed, corresponding to the intensity of light that has passed through the moist steam.

The variability quantity measuring portion 101b references the light absorption signal Sa, to calculate the variability quantity (standard deviation) a from the light absorption for a predetermined number of samples at a predetermined sampling interval. If the interval for the samples and/or the number of samples is different from when the data table or the relationship equation that show the correlation between the dryness fraction of the moist steam and the variability quantity for the light absorption, referenced by the dryness fraction measuring portion 102, were created, then the variability quantity σ is calculated through a prescribed conversion calculation.

Following this, the dryness fraction measuring portion 102 either references the correlation relationship storing portion 201d using, as the reference value, the calculated light absorption variability quantity σ, or performs a calculation based on a relationship equation, such as Equation (5), above, to output the dryness fraction χ of the moist steam, corresponding to the amount of variability in the light absorption. The dryness fraction χ of the moist steam, which has been outputted, is, for example, displayed on the outputting device 106.

Effects

Given the Further Example, explained above, the dryness fraction χ can be calculated based on the correlation relationship between the dryness fraction χ of the moist steam and the variability quantity σ of the light absorption, without being effected by the state of the moist steam, thus enabling reliable measurement of the dryness fraction of the moist steam, even when the moist steam is in a transient state.

Other Modified Examples

The present invention is not limited to the examples set forth above, but rather may be applied with a variety of modifications.

(1) For example, in the Another Example and Yet Another Example, set forth above, the structure may be one wherein the dryness fraction χ of the moist steam is measured based on the pressure p and/or the temperature t of the moist steam and on the amount of variability in the amount of light absorption, as described in the Further Example, set forth above. That is, either the correlation relationship between the dryness fraction χ of the moist steam and the variability quantity σ of the optical absorption can be stored in a data table for each measured pressure p and temperature t and then read out as appropriate, or calculations may be performed as described in Equation (6).

$$\text{Dryness fraction } \chi = g(\sigma, p, t) \qquad (6)$$

(2) Moreover, the present invention may be exemplified as a combination of the Another Example and the Yet Another Example, described above. That is, the dryness fraction measuring device may be structured so as to store the correlation relationship between the dryness fraction and the amount of variability in the intensity of light, corresponding to both the pressure p and the temperature t. That is, both the pressure p and the temperature t of the moist steam may be measured and either a data table that stores the correlation relationship for the measured pressure p and temperature t may be read out as appropriate from the correlation relationship storing portion 201, or calculations may be performed as described in Equation (7).

$$\text{Dryness fraction } \chi = f(\sigma, p, t) \qquad (7)$$

(3) Moreover, while in the examples set forth above all used water vapor as an example of moist steam, there is no limitation thereof, but rather the various examples set forth above may also be applied to the case of measuring the amount of heat in a coolant with a two-phase flow.

Area of Use in Industry

The present invention enables measured of the dryness fraction of moist steam, thus enabling application to systems and plants wherein control is carried out based on dryness fractions in a transient state.

Furthermore, the present invention can be applied also to the field of heavy industries. In this field, the dryness fraction of moist steam at a steam turbine outlet controls the efficiency of power generation, and thus it is possible to reduce the loss of heat through the ability to control the flow rate at the turbine inlet depending on the load, through measuring the dryness fraction at the turbine outlet in real-time, without waiting for stabilization of the steam (that is, through measuring the wet loss of the steam turbine).

The invention claimed is:

1. A dryness fraction measuring device, comprising:
    a variability quantity measuring portion that measures the amount of variability in intensity of light that has been transmitted, or amount of light that has been absorbed, by moist steam that is the subject of measurement;
    a dryness fraction measuring portion that measures the dryness fraction of the moist steam based on a correlation relationship between the dryness fraction and the amount of variability in the optical intensity or in the amount of light absorption; and
    a pressure measuring portion that measures a pressure of the moist steam; wherein:
    the correlation relationship is a correlation relationship between the dryness fraction and the amount of variability in the intensity of light, or in the amount of light absorbed, corresponding to a pressure of the moist steam; and
    the dryness fraction measuring portion measures the dryness fraction of the moist steam based on the correlation relationship corresponding to a measured pressure of the moist steam.

2. The dryness fraction measuring device as set forth in claim 1, further comprising:
    a temperature measuring portion that measures a temperature of the moist steam; wherein:
    the correlation relationship is a correlation relationship between the dryness fraction and the amount of variability in the intensity of light, or in the amount of light absorbed, corresponding to a temperature of the moist steam; and
    the dryness fraction measuring portion measures the dryness fraction of the moist steam based on the correlation relationship corresponding to a measured temperature of the moist steam.

3. The dryness fraction measuring device as set forth in claim 1, further comprising:
    a light-emitting portion that emits light into moist steam that is the subject of measurement;
    a light-receiving portion that receives light that has passed through the moist steam;
    an optical intensity measuring portion that measures the intensity of light received; and
    a correlation relationship storing portion that stores a correlation relationship between the dryness fraction and the amount of variability in the optical intensity for the amount of light absorbed; wherein:
    the variability quantity measuring portion measures the amount of variability in the optical intensity or in the amount of light absorbed: and
    the dryness fraction measuring portion measures the dryness fraction of the moist steam through referencing the correlation relationship stored in the correlation relationship storing portion using, as a reference value, the amount of variability in the measured optical intensity or amount of light absorbed.

* * * * *